(12) United States Patent
Ng et al.

(10) Patent No.: US 8,895,473 B2
(45) Date of Patent: Nov. 25, 2014

(54) AQUEOUS COMPOSITION FOR RAISING ANTIOXIDANT ENZYME ACTIVITIES AND ENHANCING CELL MEMBRANE-STABILITY IN PLANTS EXPOSED TO LOW TEMPERATURE

(75) Inventors: Denny Ng, Walnut, CA (US); Kai Xia, Nanjing (CN)

(73) Assignee: CH Biotech R&D Co., Ltd. (TW)

( * ) Notice: Subject to any disclaimer, the term of this patent is extended or adjusted under 35 U.S.C. 154(b) by 471 days.

(21) Appl. No.: 13/440,556

(22) Filed: Apr. 5, 2012

(65) Prior Publication Data

US 2013/0267420 A1  Oct. 10, 2013

(51) Int. Cl.
*A01N 43/08* (2006.01)
*A01N 37/44* (2006.01)
*A01N 33/12* (2006.01)
*A01N 33/08* (2006.01)

(52) U.S. Cl.
USPC ........... 504/140; 504/147; 504/148; 514/474; 514/561; 514/642

(58) Field of Classification Search
CPC ....... A01N 43/08; A01N 37/44; A01N 33/12; A01N 33/08; A01N 2300/00
USPC ........... 504/140, 147, 148; 514/474, 561, 642
See application file for complete search history.

(56) References Cited

PUBLICATIONS

Rui-Yan Sheng, Peng-Min Li, Guo-Xi Xue, Xin-Xi Zhao and Hui-Yuan Gao, "Choline Chloride Protects Cell Membrane and the Photosynthetic Apparatus in Cucumber Seedling Leaves at Low Temperature and Weak Light", Journal of Plant Physiology and Molecular Biology, 2006, 32(1), 87-93.*
Haitao Shang, Shifeng Cao, Zhenfeng Yang, Yuting Cai and Yonghua Zheng, "Effect of Exogenous γ-Aminobutyric Acid Treatment on Proline Accumulation and Chilling Injury in Peach Fruit after Long-Term Cold Storage", Journal of Agricultural and Food Chemistry, 2011, 59, 1264-1268.*
Aiping Yang, Shifeng Cao, Zhenfeng Yang, Yuting Cai and Yonghua Zheng, "gamma-Aminobutyric acid treatment reduces chilling injury and activates the defence response of peach fruit", Food Chemistry, 129 (2011), 1619-1622.*
Raina Niskanen and Ramdane Dris, "Stress responses of fruits and vegetables during storage", Journal of Food, Agriculture & Environment vol. 4 (3&4) : 202-208. 2006.*
Harsh Nayyar, Krishan Chander, Sanjeev Kumar and T. Bains, "Glycine betaine mitigates cold stress damage in Chickpea", Agronomy for Sustainable Development, 2005, 25(3), 381-388, Abstract only.*

* cited by examiner

*Primary Examiner* — John Pak
*Assistant Examiner* — Nathan W Schlientz
(74) *Attorney, Agent, or Firm* — Jen Feng Lee, Esq.

(57) ABSTRACT

Present invention provides an aqueous composition made from selected biochemical substances that will help with the low temperature tolerance of plants and thus to avoid "chilling injury" and to promote better recovery from such injury, when the solution is applied to crop plants prior to the arrival of cold snap or period of low temperature.

2 Claims, No Drawings

AQUEOUS COMPOSITION FOR RAISING ANTIOXIDANT ENZYME ACTIVITIES AND ENHANCING CELL MEMBRANE-STABILITY IN PLANTS EXPOSED TO LOW TEMPERATURE

FIELD OF THE INVENTION

The present invention relates to a foliar spray for application to plants, in anticipation of low temperature exposure, or "cold snap", which tends to cause "chilling injury" to agricultural crops.

By making the aqueous solution and the spray as disclosed herein, advance application of the spray to the plants or crops will increase the anti-oxidant enzyme activities and enhance the endurance for the injuries brought about by exposure to low temperature and also accelerate the recovery from the chilling injuries.

BACKGROUND OF THE INVENTION

Crop plants often experience a few days of cold fronts in the seasons of winter, early spring, or late fall, causing a considerable decrease in seed germination, photosynthesis, flowering and yield production.

This phenomenon of the plant injury caused by exposure to low temperature is known as "chilling injury" in the industry.

If the low temperature duration lasts for a relatively short period of time, plants can repair the damages. If the exposure is prolonged, irreversible damage usually occurs, along with visible symptoms.

Chilling injury and stress adversely affects a wide range of processes, including ethylene production, increase respiration, reduced photosynthesis, interference with energy production, accumulation of toxic compounds such as ethanol and acetaldehyde and altered cellular structure.

The primary cause of chilling injury is associated with oxidative damage at cellular level. Chilling stress induces the formation of reactive oxygen species (ROS), such as superoxide radicals ($O_2^-$) and hydrogen peroxide ($H_2O_2$), triggering a series of deleterious processes including membrane lipid peroxidation and degradation of proteins and nucleic acids in plant cells. Plants have active oxygen scavenging systems consisting of several antioxidant enzymes, including superoxide dismutase (SOD), ascorbate peroxidase (APX), catalase (CAT) and peroxidase (POX). The synchronous action of antioxidant enzymes is able to reduce the cellular ROS concentrations, thereby decrease the oxidative damage to structure of cell membrane and play a protective role during the exposure of plants to chilling stress.

Consequently, there is a need for a remedy to combat the oxidative damage at cellular level that leads to the chilling injury of the plants in such exposure to low temperature.

By making an aqueous solution mixing the selected biochemicals of Choline chloride, γ-Amino butyric acid (GABA), Ascorbic acid, and Betaine, in the proportion stated herein, the solution, when made into a spray solution by further dilution with water, will help to promote the activities of the antioxidant enzymes in plants, to help the defense against the low temperature exposure and the accelerate the needed repair and recovery from the suffered injury.

DETAILED DESCRIPTION OF THE PREFERRED EMBODIMENT

Some anti-chilling substances are found to exist in some cool-climate plants that help with the tolerance of low temperature. Tests and research showed that the known biochemical substances include proline, betaine, α-tocopherols, ascorbic acid, salicyclic acid, etc.

The antioxidant enzyme activities can be effectively raised by the proper selection and application of the chosen substances and help with plants' ability/capacity in enduring periods of low temperature.

As such, present application teaches the composition of an aqueous solution, made from diluting the composition of four (4) chemicals mixed with water, as stated below. When applied to plants a few days before the arrival of any cold snap or duration of low temperature, the activities of antioxidant enzymes in plants will be increased, and the membrane lipid damages and the content of ROS will be decreased.

The representative chemicals are briefly discussed below.

Choline Chloride:

Choline chloride has been showed to protect cell membranes in plants, which is especially important for plants to survive and growth under various environmental conditions. The young seedlings are always weak and sensitive to environment changes, so application of choline chloride showed an effect of stabling the membrane and biochemical metabolism during seed germination process.

γ-Aminobutyric Acid:

γ-aminobutyric acid (GABA) is an important neurotransmitter in the body. It is also available as a dietary supplement claimed to be useful for a variety of things, such as improving mood and promoting weight loss. In plants, GABA is a metabolite of glutamate that accumulates within the cytoplasm in response to many stresses, which suggests that GABA play roles in plant's resistance against stress conditions.

Ascorbic Acid:

Ascorbic acid is a major metabolite in plants. It is an antioxidant to protect plants against oxidative damage resulting from aerobic metabolism, photosynthesis and a range of pollutants. Ascorbic acid is also a cofactor for some hydroxylase enzymes and violaxanthin de-epoxidase. Ascorbic acid occurs in the cell wall where it is a first line of defense against ozone. Ascorbic acid also acts in control of cell division and growth.

Betaine:

Betaine is one of the major organic osmolytes that accumulate in a variety of plant species in response to environmental stresses such as drought, salinity, extreme temperatures, UV radiation and heavy metals. It is thought to have positive effects on enzyme and membrane integrity along with adaptive roles in mediating osmotic adjustment in plants grown under stress conditions:

To make the aqueous chemical composition, take a 1000-ml beaker and fill it with sufficient amount of water. Using 900 ml of water for this stated use is considered sufficient.

Add 30 grams of choline chloride, 25 grams of γ-aminobutyric acid, 50 grams of ascorbic acid and 30 grams of betaine into the 1000-ml beaker, stir the mixture to make these chemicals fully dissolved, and then add water to reach a total volume of 1,000 ml.

To make a ready-to-use spray, take the above aqueous composition and dilute with 100 times the volume of water. This diluted solution is then the ready-to-use foliar spray that will achieve the stated goals herein.

The tables submitted herein showed the test results of different plants applied with the spray solution disclosed herein, compared to a "control" set, showing the beneficial results obtained, on six (6) chilling injury measures: TBARS, $H_2O_2$, SOD activity, CAT activity, APX activity, and POX activity, as more fully explained below.

Test Result 1: Effect the Composition on Reducing Oxidative Damage to Membrane Lipids at Low Temperature Plant Materials and Treatments:

Plant seeds were soaked in 70% (v/v) ethanol for 5 minutes followed by one rinse in water, and then soaked in 0.1% (w/v) mercuric chloride for 20 minutes followed by washed with water for 3 times. Subsequently, seeds were planted in a pot containing nutrition soil. The pots were placed in a growth chamber, 70% humidity, 25±2° C. with a photoperiod of 14 hours (light intensity of 420 μmol $m^{-2}$ $s^{-1}$) and a dark period of 10 hours. At the stage of 4-5 leaves, the pots with plants were divided into three sets.

In the third set, pots with plants without chilling treatment served as control.

In the second set, the plants were sprayed with water, two days later, the pots were transferred chilling treatment to a cold chamber at 6±2° C. (light intensity of 420 μmol $m^{-2}$ $s^{-1}$) for 72 hours under 14/10 hours day/night cycle, then move back for recovery to the growth chamber at 25±2° C.

In the first set, the plants were treated with the composition solution by foliar spray, two days later, the pots were transferred chilling treatment to a cold chamber at 6±2° C. (light intensity of 420 μmol $m^{-2}$ $s^{-1}$) for 72 hours under 14/10 hours day/night cycle, then move back for recovery to the growth chamber at 25±2° C.

Determination of TBARS Content:

The plant leaves were collected after 0, 24, 48 and 72 hours of chilling and after 24 and 48 hours of the recovery period. Oxidative damage to plant membrane lipids was estimated by the formation of thiobarbituric acid reactive substances (TBARS) as the method described by Hodges etc. (Planta, 1999; 207: 604-611). 1000 mg fresh leaves are homogenized in 5 ml 120% (w/v) TCA. The homogenate is centrifuged at 3500 g for 20 minutes. To an aliquot of the supernatant (1 ml), 1 ml 20% TCA containing 0.5% (w/v) 2-thiobarbituric acid (TBA) and 4% butylated hydroxytoluene in EtOH (100 ml) are added. The mixture is heated at 95° C. for 30 minutes and then quickly cooled on ice. The contents are centrifuged at 10,000 g for 15 minutes and the absorbance is measured at 532 nm. Value for non-specific absorption at 600 nm is subtracted. The concentration of TBARS is calculated using an extinction coefficient of 155 $mM^{-1}$ $cm^{1}$.

Results:

The contents of TBARS in plants were shown in Table 1.

TABLE 1

Changes in TBARS contents (nmol $g^{-1}$FW) in leaves of control and chilling stressed plants pretreated with or without the composition. The controls for the tests are non-chilled plants. The chilling stressed plants were subjected to low temperature (6 ± 2° C.) for 72 hours and then transferred to 25 ± 2° C. at 420 μmol $m^{-2}$ $s^{-1}$ for 48 hours. The plants were treated with the composition by foliar spray 2 days before the exposure in chilling stress. Each value represents the mean ± SE of 6 replicates.

| Plant species | Group & treatment | Chilling period (6 ± 2° C.) | | | | Recovery period (25 ± 2° C.) | |
|---|---|---|---|---|---|---|---|
| | | 0 h | 24 h | 48 h | 72 h | 24 h | 48 h |
| corn | Control | 23 ± 3.2 | 18 ± 2.5 | 20 ± 2.8 | 25 ± 3.5 | 22 ± 3.0 | 26 ± 3.7 |
| | Water-chilling-recovery | 22 ± 2.6 | 45 ± 5.1 | 61 ± 5.3 | 83 ± 5.6 | 66 ± 5.8 | 55 ± 5.2 |
| | Composition-chilling-recovery | 26 ± 3.3 | 35 ± 3.0 | 42 ± 3.5 | 50 ± 4.6 | 44 ± 4.3 | 38 ± 4.0 |
| rice | Control | 26 ± 2.8 | 24 ± 2.2 | 28 ± 2.3 | 25 ± 2.3 | 27 ± 3.2 | 30 ± 3.0 |
| | Water-chilling-recovery | 23 ± 2.5 | 55 ± 4.6 | 77 ± 6.4 | 98 ± 7.8 | 82 ± 6.5 | 63 ± 5.5 |
| | Composition-chilling-recovery | 27 ± 3.2 | 33 ± 2.8 | 42 ± 3.6 | 57 ± 5.3 | 50 ± 4.5 | 42 ± 4.3 |
| wheat | Control | 18 ± 2.3 | 21 ± 2.5 | 17 ± 2.0 | 17 ± 1.8 | 22 ± 2.3 | 21 ± 2.4 |
| | Water-chilling-recovery | 17 ± 2.0 | 32 ± 2.6 | 38 ± 3.5 | 45 ± 3.6 | 36 ± 3.3 | 30 ± 3.2 |
| | Composition-chilling-recovery | 22 ± 2.4 | 27 ± 2.5 | 31 ± 2.6 | 34 ± 3.2 | 33 ± 3.0 | 29 ± 2.8 |
| barley | Control | 25 ± 2.2 | 28 ± 3.1 | 24 ± 2.5 | 26 ± 2.3 | 30 ± 2.6 | 26 ± 2.7 |
| | Water-chilling-recovery | 23 ± 2.6 | 38 ± 2.8 | 51 ± 4.6 | 67 ± 5.0 | 54 ± 5.2 | 47 ± 4.3 |
| | Composition-chilling-recovery | 26 ± 2.5 | 35 ± 2.5 | 38 ± 3.2 | 42 ± 3.6 | 35 ± 3.3 | 32 ± 3.3 |
| soybean | Control | 33 ± 2.5 | 35 ± 2.8 | 38 ± 3.1 | 33 ± 2.8 | 36 ± 3.2 | 30 ± 2.8 |
| | Water-chilling-recovery | 32 ± 2.8 | 51 ± 4.7 | 76 ± 5.9 | 92 ± 7.8 | 82 ± 7.5 | 68 ± 6.0 |
| | Composition-chilling-recovery | 35 ± 3.3 | 43 ± 3.8 | 56 ± 4.6 | 63 ± 5.6 | 55 ± 5.2 | 47 ± 5.0 |
| cucumber | Control | 25 ± 2.8 | 23 ± 2.5 | 23 ± 2.2 | 27 ± 2.3 | 29 ± 2.5 | 26 ± 2.2 |
| | Water-chilling-recovery | 27 ± 2.3 | 58 ± 4.8 | 88 ± 6.9 | 107 ± 8.6 | 94 ± 8.2 | 73 ± 7.6 |
| | Composition-chilling-recovery | 30 ± 2.6 | 45 ± 3.6 | 54 ± 4.0 | 71 ± 6.3 | 60 ± 5.5 | 58 ± 5.3 |
| tomato | Control | 33 ± 2.6 | 28 ± 2.7 | 32 ± 2.6 | 34 ± 3.0 | 28 ± 2.6 | 30 ± 2.8 |
| | Water-chilling-recovery | 32 ± 2.8 | 45 ± 3.9 | 61 ± 5.3 | 82 ± 6.6 | 72 ± 6.5 | 64 ± 6.0 |
| | Composition-chilling-recovery | 32 ± 3.1 | 37 ± 3.0 | 50 ± 4.2 | 58 ± 4.7 | 53 ± 4.5 | 45 ± 4.3 |
| pepper | Control | 25 ± 2.8 | 22 ± 2.3 | 27 ± 2.5 | 22 ± 2.5 | 25 ± 2.6 | 20 ± 2.2 |
| | Water-chilling-recovery | 24 ± 2.3 | 47 ± 4.0 | 72 ± 6.5 | 91 ± 7.6 | 82 ± 7.8 | 65 ± 6.7 |
| | Composition-chilling-recovery | 25 ± 2.4 | 40 ± 3.6 | 52 ± 4.9 | 65 ± 5.8 | 57 ± 5.5 | 47 ± 3.8 |

The data showed that the control plants without chilling stress always had a low level of TBARS in their leaves. When being exposed in chilling temperature, TBARS contents in leaves of the plants without spray of the composition (spray of water instead) quickly increased from the first to the third day in chilling period and began to decline slightly in recovery period. While treated with the composition, TBARS contents increased slowly during the chilling and recovery period and were much lower than that in the plants without treatment of the composition. The results suggest that the composition is able to reduce oxidative damage to membrane lipids and stable the plant membrane structure at chilling temperature. Reference the recorded results in Table 1.

Test Result 2: Effect the Composition on Reducing $H_2O_2$ Content in Leaves of Plants at Low Temperature.

Plant materials and treatments were as described in TEST RESULT 1.

Determination of $H_2O_2$ Content:

The $H_2O_2$ content was assayed according the methods of Mukherjee and Choudhuri (Physiologia Plantarum, 1983, 58:

166-170). 500 mg of leaves were homogenized with 3 ml of phosphate buffer (50 mm, pH 6.5) for extraction of $H_2O_2$. The homogenate was centrifuged at 6,000 g for 25 minutes. Three ml of supernatant was mixed with 1 ml of 0.1% titanium sulfate in 20% H2SO4 (v/v). The mixture was then centrifuged at 6,000 g for 10 minutes. The color intensity of the supernatant was assayed was colorimetrically at 410 nm. $H_2O_2$ content was calculated using the extinction coefficient 0.28 $\mu mol^{-1} cm^{-1}$.

Results:

The data of $H_2O_2$ content in plants were shown in Table 2.

TABLE 2

Changes in $H_2O_2$ contents (nmol $g^{-1}$FW) in leaves of control and chilling stressed plants pretreated with or without the composition. The controls for the tests are non-chilled plants. The chilling stressed plants were subjected to low temperature (6 ± 2° C.) for 72 hours and then transferred to 25 ± 2° C. at 420 μmol $m^{-2}$ $s^{-1}$ for 48 hours. The plants were treated with the composition by foliar spray 2 days before the exposure in chilling stress. Each value represents the mean ± SE of 6 replicates.

| Plant species | Group & treatment | Chilling period (6 ± 2° C.) | | | | Recovery period (25 ± 2° C.) | |
|---|---|---|---|---|---|---|---|
| | | 0 h | 24 h | 48 h | 72 h | 24 h | 48 h |
| corn | Control | 47 ± 5.5 | 52 ± 6.2 | 45 ± 5.2 | 56 ± 5.5 | 55 ± 5.8 | 50 ± 5.6 |
| | Water-chilling-recovery | 52 ± 5.0 | 122 ± 11.2 | 208 ± 25.4 | 330 ± 27.5 | 286 ± 24.3 | 230 ± 26.7 |
| | Composition-chilling-recovery | 57 ± 5.8 | 76 ± 9.6 | 124 ± 16.7 | 171 ± 21.3 | 133 ± 21.0 | 97 ± 11.2 |
| rice | Control | 75 ± 8.3 | 69 ± 7.6 | 81 ± 6.8 | 77 ± 6.9 | 65 ± 5.8 | 70 ± 6.6 |
| | Water-chilling-recovery | 72 ± 7.4 | 154 ± 17.8 | 228 ± 26.5 | 341 ± 30.6 | 303 ± 28.7 | 214 ± 23.0 |
| | Composition-chilling-recovery | 78 ± 8.2 | 126 ± 16.5 | 166 ± 18.6 | 198 ± 27.6 | 174 ± 21.3 | 128 ± 20.2 |
| wheat | Control | 55 ± 6.2 | 61 ± 6.8 | 53 ± 5.6 | 71 ± 6.5 | 65 ± 6.3 | 72 ± 6.6 |
| | Water-chilling-recovery | 60 ± 5.8 | 95 ± 10.2 | 152 ± 12.7 | 188 ± 13.5 | 163 ± 12.8 | 146 ± 13.4 |
| | Composition-chilling-recovery | 63 ± 6.0 | 83 ± 9.6 | 121 ± 10.7 | 140 ± 13.4 | 117 ± 10.6 | 90 ± 10.3 |
| barley | Control | 43 ± 3.5 | 41 ± 2.8 | 53 ± 4.4 | 47 ± 3.0 | 42 ± 3.2 | 39 ± 3.5 |
| | Water-chilling-recovery | 38 ± 3.3 | 114 ± 9.6 | 205 ± 15.6 | 276 ± 21.0 | 174 ± 13.3 | 160 ± 12.7 |
| | Composition-chilling-recovery | 45 ± 3.6 | 86 ± 6.5 | 133 ± 8.8 | 176 ± 15.2 | 145 ± 12.8 | 94 ± 8.3 |
| soybean | Control | 66 ± 5.3 | 60 ± 4.5 | 58 ± 5.2 | 62 ± 5.0 | 57 ± 5.6 | 64 ± 5.7 |
| | Water-chilling-recovery | 58 ± 5.4 | 136 ± 10.2 | 245 ± 20.4 | 323 ± 25.4 | 253 ± 23.3 | 188 ± 20.1 |
| | Composition-chilling-recovery | 63 ± 6.2 | 102 ± 8.6 | 152 ± 9.0 | 170 ± 12.5 | 124 ± 13.2 | 106 ± 11.4 |
| cucumber | Control | 85 ± 6.8 | 90 ± 7.5 | 84 ± 7.0 | 82 ± 6.8 | 92 ± 7.3 | 82 ± 7.2 |
| | Water-chilling-recovery | 96 ± 7.4 | 185 ± 23.1 | 262 ± 25.3 | 386 ± 40.3 | 240 ± 33.5 | 210 ± 26.2 |
| | Composition-chilling-recovery | 84 ± 6.4 | 133 ± 8.6 | 163 ± 16.4 | 188 ± 19.3 | 154 ± 13.7 | 142 ± 13.6 |
| tomato | Control | 45 ± 4.5 | 53 ± 4.7 | 56 ± 4.7 | 52 ± 4.2 | 47 ± 4.3 | 50 ± 4.5 |
| | Water-chilling-recovery | 52 ± 4.6 | 135 ± 12.6 | 202 ± 22.4 | 295 ± 27.5 | 230 ± 25.3 | 186 ± 20.4 |
| | Composition-chilling-recovery | 55 ± 5.0 | 86 ± 10.4 | 143 ± 16.5 | 202 ± 23.2 | 156 ± 15.4 | 106 ± 12.3 |
| pepper | Control | 57 ± 5.0 | 47 ± 4.4 | 54 ± 4.6 | 53 ± 4.0 | 50 ± 4.6 | 57 ± 4.5 |
| | Water-chilling-recovery | 46 ± 4.4 | 155 ± 18.3 | 254 ± 23.7 | 324 ± 30.2 | 270 ± 26.8 | 185 ± 22.5 |
| | Composition-chilling-recovery | 55 ± 5.1 | 98 ± 13.4 | 144 ± 15.3 | 175 ± 16.4 | 136 ± 15.3 | 122 ± 10.6 |

The data showed that the control plants without chilling stress always had a low level of $H_2O_2$ in their leaves. When being exposed in chilling temperature, $H_2O_2$ content in leaves of the plants without spray of the composition (spray of water instead) quickly increased from the first to the third day in chilling period and began to decline slightly in recovery period. While treated with the composition, $H_2O_2$ contents increased slowly during the chilling and recovery period and were much lower than that in the plants without treatment of the composition. The results suggest that the composition is able to reduce $H_2O_2$ content in leaves thus reducing the membrane lipid peroxidation at chilling temperature.

Reference the recorded result in Table 2.

Test Result 3: Effect the Composition on Increasing SOD Activity in Leaves of Plants at Low Temperature.

Plant materials and treatments were as described in TEST RESULT 1.

Extraction of Enzyme Proteins:

Three grams of plant leaves were was frozen in liquid nitrogen, ground to fine powder with a mortar under liquid nitrogen and then homogenized in 100 mM potassium phosphate buffer (pH 7.8) containing 0.1 mM ethylenediaminetetraacetic acid (EDTA), 1% (w/v) polyvinyl-pyrrolidone (PVP) and 0.5% (v/v) Triton X-100 at 4° C. The homogenate was filtered through four layers of cheesecloth and centrifuged at 15000 g for 20 min. at 4° C. The supernatant was used for determination of enzyme activities. Protein content was measured followed the method of Bradford (Analytical Biochemistry, 1976, 72: 248-254) using bovine serum albumin (BSA) as a standard.

Determination of SOD Activity:

SOD activity was determined according to the method of Beyer and Fridovich (Analytical Biochemistry, 1987, 161: 559-66). The reaction mixture contained 50 mM potassium phosphate buffer (pH 7.8), 9.9 mM methionine, 57 μM nitroblue tetrazolium (NBT) and the appropriate volume of plant extract. The reaction was initiated by light illumination. One unit of SOD is defined as the amount of enzyme, which causes a 50% decrease of the SOD inhabitable NBT reduction. NBT reduction was measured by monitoring the absorbance at 560 nm with a spectrophotometer. The activity of SOD was expressed as unit/mg protein.

Results:
The data of SOD activity in plants were shown in Table 3.

TABLE 3

Changes in SOD activity (unit/mg protein) in leaves of control and chilling stressed plants pretreated with or without the composition. The controls for the tests are non-chilled plants. The chilling stressed plants were subjected to low temperature ($6 \pm 2°$ C.) for 72 hours and then transferred to $25 \pm 2°$ C. at 420 µmol m$^{-2}$ s$^{-1}$ for 48 hours. The plants were treated with the composition by foliar spray 2 days before the exposure in chilling stress. Each value represents the mean ± SE of 6 replicates.

| Plant species | Group & treatment | Chilling period ($6 \pm 2°$ C.) | | | | Recovery period ($25 \pm 2°$ C.) | |
|---|---|---|---|---|---|---|---|
| | | 0 h | 24 h | 48 h | 72 h | 24 h | 48 h |
| corn | Control | 7 ± 0.8 | 7 ± 0.8 | 7 ± 1.0 | 8 ± 1.2 | 7 ± 0.7 | 7 ± 0.8 |
| | Water-chilling-recovery | 7 ± 1.0 | 13 ± 1.5 | 25 ± 3.2 | 33 ± 3.5 | 26 ± 3.0 | 15 ± 1.8 |
| | Composition-chilling-recovery | 7 ± 1.4 | 22 ± 2.5 | 38 ± 4.6 | 45 ± 4.0 | 28 ± 3.3 | 21 ± 2.4 |
| rice | Control | 10 ± 1.4 | 8 ± 1.3 | 10 ± 1.6 | 10 ± 1.3 | 8 ± 1.5 | 8 ± 1.2 |
| | Water-chilling-recovery | 10 ± 1.8 | 21 ± 2.6 | 30 ± 2.8 | 38 ± 3.4 | 23 ± 2.7 | 16 ± 2.3 |
| | Composition-chilling-recovery | 9 ± 1.5 | 28 ± 3.3 | 35 ± 3.6 | 47 ± 5.2 | 33 ± 3.5 | 24 ± 3.0 |
| wheat | Control | 5 ± 0.5 | 6 ± 0.5 | 6 ± 0.8 | 6 ± 0.5 | 5 ± 0.5 | 5 ± 0.8 |
| | Water-chilling-recovery | 6 ± 0.8 | 16 ± 1.8 | 33 ± 3.6 | 42 ± 3.8 | 15 ± 1.6 | 11 ± 1.0 |
| | Composition-chilling-recovery | 6 ± 0.5 | 21 ± 1.6 | 47 ± 3.9 | 49 ± 4.5 | 30 ± 3.5 | 23 ± 1.8 |
| barley | Control | 8 ± 0.6 | 6 ± 0.5 | 6 ± 0.8 | 7 ± 0.5 | 7 ± 0.7 | 8 ± 0.6 |
| | Water-chilling-recovery | 6 ± 0.6 | 15 ± 1.0 | 27 ± 2.2 | 40 ± 3.5 | 22 ± 2.6 | 15 ± 1.3 |
| | Composition-chilling-recovery | 8 ± 0.7 | 19 ± 1.6 | 32 ± 2.8 | 46 ± 3.3 | 30 ± 2.2 | 21 ± 2.0 |
| soybean | Control | 4 ± 0.3 | 4 ± 0.5 | 6 ± 0.5 | 6 ± 0.8 | 5 ± 0.8 | 4 ± 0.6 |
| | Water-chilling-recovery | 6 ± 0.6 | 14 ± 1.2 | 25 ± 1.8 | 33 ± 3.4 | 20 ± 1.7 | 12 ± 1.5 |
| | Composition-chilling-recovery | 6 ± 0.5 | 20 ± 1.8 | 28 ± 2.3 | 41 ± 3.6 | 28 ± 3.0 | 22 ± 2.4 |
| cucumber | Control | 5 ± 0.3 | 5 ± 0.6 | 5 ± 0.6 | 4 ± 0.8 | 5 ± 0.5 | 5 ± 0.6 |
| | Water-chilling-recovery | 5 ± 0.4 | 14 ± 1.7 | 20 ± 2.5 | 28 ± 2.7 | 18 ± 2.1 | 12 ± 1.5 |
| | Composition-chilling-recovery | 6 ± 0.5 | 21 ± 2.3 | 32 ± 2.6 | 36 ± 3.3 | 24 ± 2.0 | 20 ± 2.2 |
| tomato | Control | 6 ± 0.3 | 5 ± 0.5 | 6 ± 0.5 | 6 ± 0.6 | 5 ± 0.4 | 4 ± 0.7 |
| | Water-chilling-recovery | 5 ± 0.6 | 12 ± 1.6 | 25 ± 3.3 | 38 ± 4.0 | 30 ± 2.6 | 15 ± 1.4 |
| | Composition-chilling-recovery | 5 ± 0.5 | 21 ± 2.2 | 40 ± 3.7 | 55 ± 4.6 | 32 ± 3.0 | 20 ± 1.6 |
| pepper | Control | 7 ± 1.2 | 7 ± 0.8 | 5 ± 0.7 | 8 ± 0.7 | 7 ± 0.8 | 6 ± 0.8 |
| | Water-chilling-recovery | 8 ± 1.0 | 18 ± 2.2 | 30 ± 2.6 | 38 ± 3.2 | 24 ± 2.6 | 13 ± 1.5 |
| | Composition-chilling-recovery | 6 ± 0.6 | 25 ± 2.3 | 40 ± 3.5 | 43 ± 3.0 | 30 ± 3.1 | 18 ± 2.3 |

In plants, SOD acts as antioxidants and protects cellular components from being oxidized by reactive oxygen species (ROS) accumulated as a result of almost all stresses. SOD catalyzes the production of $O_2$ and $H_2O_2$ from superoxide ($O_2^-$), which results in less harmful reactants. The determination data showed that the control plants always have low SOD activity in their leave. The chilling stress induced a significant increase of SOD activity, but during the recovery period SOD activity decreased gradually. While under chilling stress, the plants with pre-treatment of the composition had even much higher SOD activity than the plants without pre-treatment of the composition. The results suggest that the composition is able to promote the increase of SOD activity in plants under chilling stress thus protects cellular components from being oxidized.

Reference the recorded result in Table 3.

Test Result 4: Effect the Composition on Increasing CAT Activity in Leaves of Plants at Low Temperature.

Plant materials and treatments were as described in TEST RESULT 1.

Extraction of enzyme proteins was as described in TEST RESULT 3.

Determination of CAT Activity:

CAT activity was determined by monitoring the decomposition of $H_2O_2$ (extinction coefficient 39.4 mM cm$^{-1}$) at 240 nm according to the method of Aebi (Methods of Enzymatic Analysis, Vol. 2, pp: 673-684. Academic Press, NY, 1974). The reaction mixture contained 50 mM potassium phosphate buffer (pH 7.0) and plant extract in a 3 ml volume. The reaction was initiated by adding 10 mM $H_2O_2$. One unit of CAT is defined as the amount of enzyme, which liberates half the peroxide oxygen from 10 mm $H_2O_2$ solution in 100 seconds at 25° C.

Results:

The data of CAT activity in plants were shown in Table 4.

TABLE 4

Changes in CAT activity (unit/mg protein) in leaves of control and chilling stressed plants pretreated with or without the composition. The controls for the tests are non-chilled plants. The chilling stressed plants were subjected to low temperature ($6 \pm 2°$ C.) for 72 hours and then transferred to $25 \pm 2°$ C. at 420 µmol m$^{-2}$ s$^{-1}$ for 48 hours. The plants were treated with the composition by foliar spray 2 days before the exposure in chilling stress. Each value represents the mean ± SE of 6 replicates.

| Plant species | Group & treatment | Chilling period ($6 \pm 2°$ C.) | | | | Recovery period ($25 \pm 2°$ C.) | |
|---|---|---|---|---|---|---|---|
| | | 0 h | 24 h | 48 h | 72 h | 24 h | 48 h |
| corn | Control | 4 ± 0.3 | 4 ± 0.5 | 4 ± 0.5 | 4 ± 0.3 | 4 ± 0.5 | 4 ± 0.5 |
| | Water-chilling-recovery | 4 ± 0.5 | 6 ± 0.6 | 7 ± 0.6 | 8 ± 0.7 | 10 ± 1.5 | 10 ± 1.2 |
| | Composition-chilling-recovery | 5 ± 0.5 | 10 ± 0.8 | 9 ± 0.6 | 11 ± 1.3 | 16 ± 1.2 | 14 ± 1.3 |

TABLE 4-continued

Changes in CAT activity (unit/mg protein) in leaves of
control and chilling stressed plants pretreated with or without the composition.
The controls for the tests are non-chilled plants. The chilling stressed plants
were subjected to low temperature (6 ± 2° C.) for 72 hours and then transferred to 25 ± 2° C. at
420 µmol m$^{-2}$ s$^{-1}$ for 48 hours. The plants were treated with the composition by foliar spray 2 days
before the exposure in chilling stress. Each value represents the mean ± SE of 6 replicates.

| Plant species | Group & treatment | Chilling period (6 ± 2° C.) | | | | Recovery period (25 ± 2° C.) | |
|---|---|---|---|---|---|---|---|
| | | 0 h | 24 h | 48 h | 72 h | 24 h | 48 h |
| rice | Control | 2 ± 0.4 | 3 ± 0.3 | 3 ± 0.4 | 2 ± 0.3 | 2 ± 0.4 | 3 ± 0.3 |
| | Water-chilling-recovery | 2 ± 0.3 | 4 ± 0.5 | 5 ± 0.4 | 4 ± 0.4 | 7 ± 0.5 | 6 ± 0.6 |
| | Composition-chilling-recovery | 2 ± 0.4 | 6 ± 0.7 | 8 ± 0.6 | 7 ± 0.6 | 12 ± 1.0 | 9 ± 0.8 |
| wheat | Control | 4 ± 0.5 | 3 ± 0.4 | 3 ± 0.5 | 4 ± 0.4 | 2 ± 0.3 | 3 ± 0.3 |
| | Water-chilling-recovery | 3 ± 0.4 | 4 ± 0.4 | 6 ± 0.5 | 5 ± 0.5 | 12 ± 0.8 | 10 ± 0.8 |
| | Composition-chilling-recovery | 4 ± 0.5 | 7 ± 0.6 | 9 ± 0.6 | 10 ± 0.8 | 17 ± 1.4 | 14 ± 1.5 |
| barley | Control | 1 ± 0.3 | 2 ± 0.3 | 1 ± 0.2 | 1 ± 0.3 | 2 ± 0.5 | 2 ± 0.3 |
| | Water-chilling-recovery | 1 ± 0.2 | 2 ± 0.4 | 3 ± 0.4 | 3 ± 0.5 | 7 ± 0.8 | 7 ± 0.5 |
| | Composition-chilling-recovery | 1 ± 0.3 | 3 ± 0.4 | 6 ± 0.5 | 5 ± 0.3 | 12 ± 0.9 | 11 ± 1.0 |
| soybean | Control | 4 ± 0.6 | 4 ± 0.6 | 4 ± 0.4 | 5 ± 0.5 | 3 ± 0.4 | 4 ± 0.4 |
| | Water-chilling-recovery | 3 ± 0.5 | 5 ± 0.7 | 8 ± 0.6 | 8 ± 0.7 | 12 ± 0.8 | 13 ± 1.1 |
| | Composition-chilling-recovery | 4 ± 0.6 | 8 ± 0.7 | 13 ± 1.0 | 15 ± 1.2 | 19 ± 2.2 | 16 ± 1.2 |
| cucumber | Control | 5 ± 0.4 | 4 ± 0.3 | 4 ± 0.4 | 4 ± 0.3 | 5 ± 0.5 | 5 ± 0.4 |
| | Water-chilling-recovery | 5 ± 0.6 | 6 ± 0.5 | 7 ± 0.5 | 7 ± 0.8 | 9 ± 0.8 | 81 ± 0.7 |
| | Composition-chilling-recovery | 4 ± 0.3 | 8 ± 0.6 | 10 ± 0.7 | 8 ± 0.8 | 14 ± 1.2 | 12 ± 0.8 |
| tomato | Control | 3 ± 0.3 | 3 ± 0.3 | 4 ± 0.7 | 5 ± 0.6 | 4 ± 0.4 | 4 ± 0.6 |
| | Water-chilling-recovery | 5 ± 0.4 | 6 ± 0.6 | 8 ± 0.7 | 6 ± 0.5 | 10 ± 0.6 | 10 ± 0.9 |
| | Composition-chilling-recovery | 3 ± 0.2 | 10 ± 1.1 | 13 ± 1.2 | 10 ± 0.8 | 16 ± 1.4 | 15 ± 1.0 |
| pepper | Control | 3 ± 0.3 | 3 ± 0.2 | 4 ± 0.5 | 3 ± 0.3 | 4 ± 02 | 4 ± 0.4 |
| | Water-chilling-recovery | 4 ± 0.3 | 6 ± 0.4 | 5 ± 0.3 | 6 ± 0.5 | 9 ± 0.7 | 9 ± 0.9 |
| | Composition-chilling-recovery | 4 ± 0.5 | 9 ± 0.6 | 7 ± 0.5 | 9 ± 0.8 | 14 ± 1.6 | 13 ± 1.5 |

CAT is mostly located in a cellular organelle called the peroxisome, and it mediates the breakdown of $H_2O_2$ caused by stresses. The determination data showed that the control plants always have low CAT activity in their leave. Plants exposed to chilling temperature had an increase of CAT activity, and an even higher increase of CAT activity at the recovery period. Under chilling stress, the plants with pre-treatment of the composition had much higher CAT activity than the plants without pre-treatment of the composition at both chilling and recovery period. The results suggest that the composition is able to induce the increase of CAT activity in plants under chilling stress for reducing $H_2O_2$ accumulation in leaves thus preventing the membrane lipid peroxidation at chilling temperature.

Reference the recorded result in Table 4.

Test Result 5: Effect the Composition on Increasing APX Activity in Leaves of Plants at Low Temperature.

Plant materials and treatments were as described in TEST RESULT 1.

Extraction of Enzyme Proteins:

Three grams of plant leaves were was frozen in liquid nitrogen, ground to fine powder with a mortar under liquid nitrogen and then homogenized in homogenized in 100 mM sodium phosphate buffer (pH 7.0) containing 5 mm ascorbate and 1 mm EDTA. The homogenate was filtered through four layers of cheesecloth and centrifuged at 18000 g for 20 min. at 4° C. The supernatant was used for determination of antioxidant enzyme activities. Protein content was measured according to the method of Lowry et al. (1951) with bovine serum albumin (BSA) as a standard.

Determination of APX Activity:

APX activity was determined as a decrease in absorbance at 290 nm for 1 minutes as described by Nakano and Asada (Plant Cell Physiology, 1981, 22: 867-880). The reaction mixture contained 50 mM potassium phosphate buffer (pH 7.0), 0.5 mM ascorbate, 0.1 mM $H_2O_2$, 0.1 mM EDTA and 0.5 ml plant extract in a 3 ml volume.

Results:

The data of APX activity in plants were shown in Table 5.

TABLE 5

Changes in APX activity (µmol $H_2O_2$ mim$^{-1}$ mg$^{1-}$ protein) in leaves of control and chilling stressed
The controls for the tests are non-chilled plants. The chilling stressed plants were subjected to low temperature
(6 ± 2° C.) for 72 hours and then transferred to 25 ± 2° C. at 420 µmol m$^{-2}$ s$^{-1}$ for 48 hours. The plants were
treated with the composition by foliar spray 2 days before the exposure in chilling stress. Each value represents
the mean ± SE of 6 replicates.
plants pretreated with or without the composition.

| Plant species | Group & treatment | Chilling period (6 ± 2° C.) | | | | Recovery period (25 ± 2° C.) | |
|---|---|---|---|---|---|---|---|
| | | 0 h | 24 h | 48 h | 72 h | 24 h | 48 h |
| corn | Control | 0.3 ± 0.05 | 0.3 ± 0.07 | 0.2 ± 0.04 | 0.2 ± 0.05 | 0.3 ± 0.07 | 0.3 ± 0.06 |
| | Water-chilling-recovery | 0.3 ± 0.05 | 0.5 ± 0.05 | 0.4 ± 0.06 | 0.4 ± 0.05 | 0.7 ± 0.04 | 0.8 ± 0.07 |
| | Composition-chilling-recovery | 0.3 ± 0.04 | 0.6 ± 0.06 | 0.8 ± 0.07 | 0.8 ± 0.06 | 1.0 ± 0.11 | 1.1 ± 0.09 |

TABLE 5-continued

Changes in APX activity ($\mu$mol $H_2O_2$ mim$^{-1}$ mg$^{1-}$ protein) in leaves of control and chilling stressed
The controls for the tests are non-chilled plants. The chilling stressed plants were subjected to low temperature
(6 ± 2° C.) for 72 hours and then transferred to 25 ± 2° C. at 420 $\mu$mol m$^{-2}$ s$^{-1}$ for 48 hours. The plants were
treated with the composition by foliar spray 2 days before the exposure in chilling stress. Each value represents
the mean ± SE of 6 replicates.
plants pretreated with or without the composition.

| Plant species | Group & treatment | Chilling period (6 ± 2° C.) | | | | Recovery period (25 ± 2° C.) | |
|---|---|---|---|---|---|---|---|
| | | 0 h | 24 h | 48 h | 72 h | 24 h | 48 h |
| rice | Control | 0.3 ± 0.04 | 0.3 ± 0.05 | 0.4 ± 0.06 | 0.3 ± 0.03 | 0.4 ± 0.06 | 0.4 ± 0.05 |
| | Water-chilling-recovery | 0.4 ± 0.06 | 0.4 ± 0.04 | 0.6 ± 0.08 | 0.5 ± 0.05 | 0.7 ± 0.06 | 0.6 ± 0.05 |
| | Composition-chilling-recovery | 0.4 ± 0.05 | 0.5 ± 0.07 | 0.9 ± 0.07 | 0.7 ± 0.08 | 0.9 ± 0.07 | 1.2 ± 0.11 |
| wheat | Control | 0.5 ± 0.03 | 0.6 ± 0.05 | 0.5 ± 0.04 | 0.5 ± 0.04 | 0.5 ± 0.05 | 0.6 ± 0.04 |
| | Water-chilling-recovery | 0.5 ± 0.05 | 0.7 ± 0.06 | 0.8 ± 0.08 | 0.7 ± 0.05 | 1.0 ± 0.07 | 0.9 ± 0.08 |
| | Composition-chilling-recovery | 0.6 ± 0.05 | 0.9 ± 0.09 | 1.0 ± 0.06 | 0.9 ± 0.07 | 1.2 ± 0.10 | 1.3 ± 0.15 |
| barley | Control | 0.4 ± 0.06 | 0.3 ± 0.04 | 0.4 ± 0.05 | 0.4 ± 0.05 | 0.3 ± 0.04 | 0.3 ± 0.04 |
| | Water-chilling-recovery | 0.3 ± 0.03 | 0.5 ± 0.06 | 0.6 ± 0.05 | 0.6 ± 0.07 | 0.8 ± 0.05 | 1.0 ± 0.08 |
| | Composition-chilling-recovery | 0.3 ± 0.04 | 0.7 ± 0.06 | 0.9 ± 0.08 | 0.8 ± 0.06 | 1.2 ± 0.13 | 1.4 ± 0.15 |
| soybean | Control | 0.2 ± 0.02 | 0.2 ± 0.01 | 0.2 ± 0.02 | 0.3 ± 0.02 | 0.3 ± 0.05 | 0.2 ± 0.04 |
| | Water-chilling-recovery | 0.3 ± 0.05 | 0.3 ± 0.04 | 0.5 ± 0.04 | 0.5 ± 0.05 | 0.6 ± 0.04 | 0.7 ± 0.06 |
| | Composition-chilling-recovery | 0.3 ± 0.03 | 0.6 ± 0.05 | 0.7 ± 0.07 | 0.9 ± 0.08 | 1.0 ± 0.07 | 1.1 ± 0.08 |
| cucumber | Control | 0.2 ± 0.02 | 0.2 ± 0.01 | 0.3 ± 0.04 | 0.1 ± 0.01 | 0.2 ± 0.03 | 0.3 ± 0.02 |
| | Water-chilling-recovery | 0.1 ± 0.02 | 0.3 ± 0.05 | 0.5 ± 0.06 | 0.6 ± 0.05 | 0.7 ± 0.06 | 0.6 ± 0.04 |
| | Composition-chilling-recovery | 0.2 ± 0.03 | 0.4 ± 0.04 | 0.7 ± 0.08 | 0.7 ± 0.06 | 1.0 ± 0.08 | 1.2 ± 0.11 |
| tomato | Control | 0.4 ± 0.03 | 0.5 ± 0.04 | 0.5 ± 0.07 | 0.4 ± 0.04 | 0.5 ± 0.07 | 0.5 ± 0.06 |
| | Water-chilling-recovery | 0.5 ± 0.07 | 0.5 ± 0.07 | 0.7 ± 0.07 | 0.4 ± 0.06 | 0.8 ± 0.09 | 0.8 ± 0.07 |
| | Composition-chilling-recovery | 0.4 ± 0.05 | 0.6 ± 0.08 | 0.9 ± 0.08 | 0.8 ± 0.06 | 1.2 ± 0.10 | 1.3 ± 0.18 |
| pepper | Control | 0.4 ± 0.06 | 0.5 ± 0.05 | 0.5 ± 0.06 | 0.6 ± 0.07 | 0.4 ± 0.03 | 0.5 ± 0.04 |
| | Water-chilling-recovery | 0.5 ± 0.07 | 0.6 ± 0.06 | 0.8 ± 0.05 | 0.7 ± 0.06 | 0.9 ± 0.07 | 1.1 ± 0.08 |
| | Composition-chilling-recovery | 0.5 ± 0.06 | 0.8 ± 0.09 | 1.1 ± 0.07 | 1.2 ± 0.10 | 1.4 ± 0.15 | 1.5 ± 0.17 |

APX is mainly located in chloroplasts and able to detoxify peroxides such as $H_2O_2$ using ascorbate as a substrate. The determination data showed that the control plants always have low APX activity in their leave. Plants exposed to chilling temperature had a slight increase of APX activity, and a huge increase of APX activity at the recovery period. Under chilling stress, the plants with pre-treatment of the composition had much higher APX activity than the plants without pre-treatment of the composition at both chilling and recovery period. The results suggest that the composition is able to induce the increase of APX activity in plants under chilling stress for breaking $H_2O_2$ down in leaf chloroplasts thus reducing the photosynthetic chloroplast membrane damage at chilling temperature.

Reference the recorded result in Table 5.

Test Result 6: Effect the Composition on Increasing POX Activity in Leaves of Plants at Low Temperature.

Plant materials and treatments were as described in TEST RESULT 1.

Extraction of enzyme proteins was as described in TEST RESULT 3.

Determination of POX Activity:

POX activity was determined as described by Scebba et al (Journal of Plant Physiology, 1999, 155: 762-768). The reaction mixture contained 10 mM phosphate buffer (pH 7.0), 10 mM $H_2O_2$, 20 mM guaiacol and 0.5 mL enzyme extract in a 3 ml volume. The POX activity was assayed by monitoring the increase in absorbance at 470 nm due to guaiacol oxidation.

Results:

The data of POX activity in plants were shown in Table 6.

TABLE 6

Changes in POX activity ($\mu$mol $H_2O_2$ mim$^{-1}$ mg$^{1-}$ protein) in leaves of control and chilling
stressed plants pretreated with or without the composition. The controls for the tests are
non-chilled plants. The chilling stressed plants were subjected to low temperature
(6 ± 2° C.) for 72 hours and then transferred to 25 ± 2° C. at 420 $\mu$mol m$^{-2}$ s$^{-1}$
for 48 hours. The plants were treated with the composition by foliar spray 2 days before
the exposure in chilling stress. Each value represents the mean ± SE of 6 replicates.

| Plant species | Group & treatment | Chilling period (6 ± 2° C.) | | | | Recovery period (25 ± 2° C.) | |
|---|---|---|---|---|---|---|---|
| | | 0 h | 24 h | 48 h | 72 h | 24 h | 48 h |
| corn | Control | 0.2 ± 0.02 | 0.2 ± 0.03 | 0.2 ± 0.03 | 0.1 ± 0.02 | 0.2 ± 0.02 | 0.2 ± 0.03 |
| | Water-chilling-recovery | 0.2 ± 0.03 | 0.4 ± 0.05 | 0.8 ± 0.07 | 0.7 ± 0.05 | 0.5 ± 0.05 | 0.3 ± 0.04 |
| | Composition-chilling-recovery | 0.2 ± 0.03 | 0.5 ± 0.05 | 1.1 ± 0.09 | 1.0 ± 0.10 | 0.7 ± 4.06 | 0.4 ± 0.06 |
| rice | Control | 0.1 ± 0.01 | 0.2 ± 0.03 | 0.1 ± 0.02 | 0.1 ± 0.02 | 0.2 ± 0.04 | 0.2 ± 0.03 |
| | Water-chilling-recovery | 0.2 ± 0.03 | 0.4 ± 0.06 | 0.6 ± 0.05 | 0.6 ± 0.08 | 0.3 ± 0.03 | 0.2 ± 0.04 |
| | Composition-chilling-recovery | 0.1 ± 0.02 | 0.6 ± 0.08 | 1.0 ± 0.05 | 0.9 ± 0.06 | 0.4 ± 0.04 | 0.2 ± 0.04 |

TABLE 6-continued

Changes in POX activity (μmol H$_2$O$_2$ mim$^{-1}$ mg$^{1-}$ protein) in leaves of control and chilling stressed plants pretreated with or without the composition. The controls for the tests are non-chilled plants. The chilling stressed plants were subjected to low temperature (6 ± 2° C.) for 72 hours and then transferred to 25 ± 2° C. at 420 μmol m$^{-2}$ s$^{-1}$ for 48 hours. The plants were treated with the composition by foliar spray 2 days before the exposure in chilling stress. Each value represents the mean ± SE of 6 replicates.

| Plant species | Group & treatment | Chilling period (6 ± 2° C.) | | | | Recovery period (25 ± 2° C.) | |
|---|---|---|---|---|---|---|---|
| | | 0 h | 24 h | 48 h | 72 h | 24 h | 48 h |
| wheat | Control | 0.4 ± 0.03 | 0.3 ± 0.03 | 0.4 ± 0.05 | 0.4 ± 0.04 | 0.4 ± 0.05 | 0.4 ± 0.05 |
| | Water-chilling-recovery | 0.4 ± 0.05 | 0.6 ± 0.06 | 0.9 ± 0.08 | 0.6 ± 0.04 | 0.6 ± 4.07 | 0.4 ± 0.05 |
| | Composition-chilling-recovery | 0.4 ± 0.05 | 0.7 ± 0.05 | 1.3 ± 0.11 | 1.2 ± 0.08 | 0.8 ± 4.08 | 0.5 ± 0.07 |
| barley | Control | 0.3 ± 0.02 | 03 ± 0.02 | 0.4 ± 0.03 | 0.3 ± 0.04 | 0.4 ± 0.03 | 0.3 ± 0.03 |
| | Water-chilling-recovery | 0.4 ± 0.04 | 0.7 ± 0.05 | 1.0 ± 0.09 | 1.1 ± 0.08 | 0.8 ± 0.07 | 0.6 ± 0.07 |
| | Composition-chilling-recovery | 0.4 ± 0.03 | 0.8 ± 0.06 | 1.3 ± 0.12 | 1.2 ± 0.13 | 1.0 ± 0.08 | 0.6 ± 0.05 |
| soybean | Control | 0.3 ± 0.05 | 0.4 ± 0.04 | 0.3 ± 0.04 | 0.3 ± 0.03 | 0.3 ± 0.04 | 0.4 ± 0.06 |
| | Water-chilling-recovery | 0.3 ± 0.03 | 0.5 ± 0.05 | 0.8 ± 0.06 | 0.7 ± 0.05 | 0.4 ± 0.04 | 0.4 ± 0.05 |
| | Composition-chilling-recovery | 0.3 ± 0.05 | 0.6 ± 0.07 | 1.1 ± 0.08 | 1.0 ± 0.04 | 0.7 ± 0.05 | 0.6 ± 0.08 |
| cucumber | Control | 0.2 ± 0.04 | 0.2 ± 0.04 | 0.2 ± 0.03 | 0.2 ± 0.04 | 0.1 ± 0.02 | 0.2 ± 0.03 |
| | Water-chilling-recovery | 0.2 ± 0.03 | 0.3 ± 0.03 | 0.6 ± 0.05 | 0.7 ± 0.05 | 0.6 ± 0.04 | 0.3 ± 0.03 |
| | Composition-chilling-recovery | 0.2 ± 0.03 | 0.5 ± 0.04 | 0.9 ± 0.06 | 0.9 ± 0.08 | 0.7 ± 0.06 | 0.5 ± 0.06 |
| tomato | Control | 0.3 ± 0.06 | 0.3 ± 0.04 | 0.4 ± 0.06 | 0.3 ± 0.05 | 0.4 ± 0.04 | 0.3 ± 0.04 |
| | Water-chilling-recovery | 0.4 ± 0.05 | 0.5 ± 0.07 | 0.9 ± 0.06 | 1.1 ± 0.08 | 0.9 ± 0.09 | 0.5 ± 0.06 |
| | Composition-chilling-recovery | 0.4 ± 0.05 | 0.8 ± 0.06 | 1.3 ± 0.09 | 1.4 ± 0.12 | 1.1 ± 0.07 | 0.8 ± 0.07 |
| pepper | Control | 0.3 ± 0.05 | 0.2 ± 0.03 | 0.3 ± 0.04 | 0.3 ± 0.02 | 0.2 ± 0.03 | 0.2 ± 0.04 |
| | Water-chilling-recovery | 0.3 ± 0.04 | 0.4 ± 0.05 | 0.7 ± 0.08 | 0.6 ± 0.06 | 0.4 ± 0.03 | 0.2 ± 0.02 |
| | Composition-chilling-recovery | 0.2 ± 0.05 | 0.7 ± 0.06 | 1.0 ± 0.09 | 0.9 ± 0.09 | 0.8 ± 0.07 | 0.4 ± 0.05 |

POX is localized in peroxisomes and decomposes H$_2$O$_2$ using phenolic compounds as substrates. The determination data showed that the control plants always have low POX activity in their leave. Under chilling stress, POX activity in leaves increased remarkably at 3 days chilling period, and then decreased at 2 days recovery period. The plants with pre-treatment of the composition had much higher POX activity than the plants without pre-treatment of the composition mainly at chilling period. The results suggest that the composition is able to induce the increase of POX activity in plants during chilling period for reducing H$_2$O$_2$ accumulation in leaves thus preventing the membrane lipid peroxidation at chilling temperature.

The invention claimed is:

1. An aqueous composition for raising antioxidant enzyme activities in plants, comprising:
   a. 30 grams of choline chloride;
   b. 25 grams of γ-aminobutyric acid;
   c. 50 grams of ascorbic acid; and
   d. 30 grams of betaine;
   dissolved in water to a total volume of 1 liter.

2. A ready-for-use spray solution comprising:
   a. 30 grams of choline chloride;
   b. 25 grams of γ-aminobutyric acid;
   c. 50 grams of ascorbic acid; and
   d. 30 grams of betaine;
   dissolved in water to a total volume of 100 liters.

* * * * *